United States Patent
Kottenstette et al.

(10) Patent No.: US 6,663,697 B1
(45) Date of Patent: Dec. 16, 2003

(54) MICROFABRICATED PACKED GAS CHROMATOGRAPHIC COLUMN

(75) Inventors: Richard Kottenstette, Albuquerque, NM (US); Carolyn M. Matzke, Los Lunas, NM (US); Gregory C. Frye-Mason, Cedar Crest, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 10/165,862

(22) Filed: Jun. 6, 2002

Related U.S. Application Data (60) Provisional application No. 60/336,546, filed on Nov. 2, 2001, and provisional application No. 60/336,127, filed on Nov. 2, 2001.

(51) Int. Cl.[7] ............................................. B01D 15/08
(52) U.S. Cl. ........................ 96/101; 73/23.39; 96/105; 96/107
(58) Field of Search .................... 73/23.35, 23.39; 95/82, 85, 87, 88; 96/101–107

(56) References Cited

U.S. PATENT DOCUMENTS

| | | | | |
|---|---|---|---|---|
| 3,016,106 A | * | 1/1962 | Luft ............................ 96/101 |
| 3,149,941 A | * | 9/1964 | Barnitz et al. ................. 96/101 |
| 3,319,403 A | * | 5/1967 | Rose et al. .................... 96/101 |
| 3,449,938 A | * | 6/1969 | Giddings ...................... 73/23.39 |
| 3,503,712 A | * | 3/1970 | Sussman ....................... 422/191 |
| 3,538,744 A | * | 11/1970 | Karasek ....................... 73/23.39 |
| 3,630,006 A | * | 12/1971 | Sandoval ...................... 96/101 |
| 3,748,833 A | * | 7/1973 | Karas et al. ................... 96/105 |
| 4,116,836 A | * | 9/1978 | DeAngelis ..................... 210/198.2 |
| 4,350,586 A | * | 9/1982 | Conlon et al. ................. 210/149 |
| 4,935,040 A | * | 6/1990 | Goedert ........................ 73/23.22 |
| 4,960,444 A | * | 10/1990 | Ghaoui ......................... 95/88 |
| 5,132,012 A | * | 7/1992 | Miura et al. ................... 210/198.2 |
| 5,376,252 A | * | 12/1994 | Ekstrom et al. ................ 204/603 |
| 5,544,276 A | * | 8/1996 | Loux et al. .................... 392/480 |
| 5,611,846 A | * | 3/1997 | Overton et al. ................ 96/102 |
| 5,792,943 A | * | 8/1998 | Craig .......................... 73/61.52 |
| 5,997,708 A | * | 12/1999 | Craig .......................... 204/601 |
| 6,068,684 A | * | 5/2000 | Overton ........................ 96/104 |
| 6,068,780 A | * | 5/2000 | Yu ............................. 216/10 |
| 6,074,725 A | * | 6/2000 | Kennedy ....................... 428/188 |
| 6,171,378 B1 | * | 1/2001 | Manginell et al. .............. 96/143 |
| 6,296,685 B1 | * | 10/2001 | Cammann et al. ............... 95/45 |
| 6,454,840 B1 | * | 9/2002 | Gellert et al. ................. 96/101 |
| 6,497,138 B1 | * | 12/2002 | Abdel-Rahman et al. ......... 73/23.42 |

* cited by examiner

Primary Examiner—Robert H. Spitzer
(74) Attorney, Agent, or Firm—Kevin W. Bieg; Brian W. Dodson (57) ABSTRACT

A new class of miniaturized gas chromatographic columns has been invented. These chromatographic columns are formed using conventional micromachining techniques, and allow packed columns having lengths on the order of a meter to be fabricated with a footprint on the order of a square centimeter.

14 Claims, 7 Drawing Sheets

MICROFABRICATED PACKED GAS CHROMATOGRAPHIC COLUMN

COPENDING APPLICATIONS

The instant application claims the priority of previously filed Provisional Application No. 60/336,546, filed by the instant inventors on Nov. 2, 2001. The instant application is also related to copending U.S. patent application Ser. No. (#09/396,660), filed on Sep. 9, 1999, by Stephen A. Calalnuovo, Gregory C. Frye-Mason, Ronald Manginell, and Carloyn M. Matzke. The instant application is also related to copending U.S. Provisional Application No. 60/336,127, filed on Nov. 2, 2001 by the instant inventors. The instant application is also related to copending U.S. patent application (#10/061,383), filed on Jan. 1, 2002, by Ronald Manginell and Gregory C. Frye-Mason. These copending applications have been assigned to Sandia Corporation, as has the instant application.

GOVERNMENT RIGHTS

This invention was made with Government support under Contract DE-AC0494AL85000 awarded by the U.S. Department of Energy. The Government has certain rights in this invention.

FIELD OF THE INVENTION

The present invention relates generally to apparatus for gas chromatography, and more specifically to microfabricated gas chromatographic columns designed for effective packing with particulate chromatographic media.

BACKGROUND OF THE INVENTION

Analysis of chemical samples has long been carried out using gas chromatography. Generally, gas chromatography involves separation of chemical species transported in a mobile gas phase in which the chemical species, called analytes, are volatized and carried along by the mobile phase. The mobile phase is forced through or past a stationary phase which is typically a polymer film or a porous film or particle.

The chemical species of interest will have different affinities for the stationary phase, as well as different vapor pressures (tendency to be in the vapor or mobile phase). As the mobile phase is forced through and/or past the stationary phase, the analytes are retained to different degrees in the stationary phase, resulting in different effective velocities through the column, the net result being separation of the chemical species in the sample.

In a common approach to gas chromatography, narrow tubes called columns are packed with a particulate stationary phase, through which the mobile phase is forced. A sample of the chemical species to be separated is typically injected into such a column along with a small amount of the mobile phase. Then the sample is transported through the column by continuous addition of pure mobile phase.

The average rate at which an analyte moves through is determined by the flow rate of the mobile phase, the affinity the analyte has with the stationary phase, and the vapor pressure of the analyte. When the analyte emerges from the column, the elution time is determined using a detector. This elution time provides considerable information about the nature of the analyte.

In some cases the detector simply signals the presence of some material in the eluent other than the mobile phase itself, while in other cases the detector provides additional information about the chemical makeup of the analyte (for example, when a portion of the eluent is directed into a mass spectrograph).

Many types of stationary phases are used in chromatographic analysis. These can have a variety of physicochemical properties, and can also take different physical forms. In the simplest form, the stationary phase is simply a solid or a collection of solid particles, and the analyte is adsorbed on the surface of the solid making up the stationary phase.

More commonly, though, the surface of the stationary phase material is altered to obtain a desired chemical affinity. This alteration can involve coating a solid support with a thin liquid phase, in which the analyte alternately is sorbed and released from the thin liquid phase as the mobile phase moves over the stationary phase. A stationary phase can be altered by covalently attaching molecules thereto which have a special affinity (or lack thereof) for certain chemical species of interest. Many other examples are known in the art.

Gas chromatographic columns are usually based upon open tubular columns or on tubular packed beds. Open tubular columns are typically about 0.1–0.5 millimeters in inside diameter and 5 to 30 meters in length, with a submicron polymer layer on the inside of the tube making up the stationary phase. Tubular packed beds are typically about 3 millimeters in inside diameter and 2–3 meters in length, and are filled with a solid powder whose porous surfaces or surface coating forms the stationary phase.

Gas chromatographic columns must have considerable length to provide adequate separation of analytes. However, there is a high cost to be paid in providing such long columns. Typically the column must be maintained at a constant and elevated temperature, which requires a large heated and insulated enclosure whose operation may require hundreds to thousands of watts for operation. Long columns are often fragile as well, which limits their potential utility.

There are many potential applications for chromatographic analysis which would greatly benefit from development and implementation of smaller and more thermally efficient chromatographic columns. Among these would be included process control, industrial hygiene, environmental analysis, portable chemical analysis equipment, first responder tools, point-of-care diagnostics, and many more. As a result, there is a long-felt need for chromatographic columns which provide a long column length within a small column footprint, volume, and power requirement.

There have been previous examples of miniature chromatographic columns built using microfabrication techniques based on silicon lithography similar to those used to fabricate LIGA and microelectromechanical systems (MEMS).

The prior art includes description of a microfabricated column for gas chromatography which comprises a high aspect ratio channel in the form of a spiral on a silicon substrate. When formed, the grooves are open at the surface of the silicon substrate. The grooves are coated with a thin polymer stationary phase, and then the channel is sealed by attaching a Pyrex cover to the surface of the silicon substrate.

This microfabricated gas chromatographic column is in function, if not in specific structure, a miniature version of the conventional open tubular column. Such columns are useful for separation of certain types of volatile and semi-volatile analytes. However, the use of a thin polymer stationary phase combined with the relatively short length of the microfabricated column (roughly one meter compared to the conventional 5 to 30 meters) significantly limits the separation ability of this prior art microfabricated column, especially for analysis of gaseous mixtures.

There is thus a need for a miniature analog of the tubular packed bed gas chromatographic column. The use of a packed particulate stationary phase provides much larger surface area than is possible through use of a thin polymer stationary phase. In addition, the tortuous path which must be taken by the mobile phase through a packed particulate stationary phase in a tubular packed bed leads to more effective analyte separation in a given column length.

SUMMARY OF THE INVENTION

A new type of miniature packed gas chromatographic column has been invented. These columns are fabricated by sealing a cover plate onto a substrate whose surface is configured so as to form an elongated column comprising a packing retainer which serves to retain a particulate chromatographic medium within the column. These columns achieve effective and rapid analyte separation with a very small footprint and desirable thermal characteristics.

BRIEF DESCRIPTION OF THE ILLUSTRATIONS

DETAILED DESCRIPTION

A number of specific implementations of the instant invention are described herein, with the intent of illustrating various features and benefits of the instant invention. The choice of these specific implementations over others is not intended to limit the scope of the invention, which is set by the claims in view of the specification and the drawings.

The instant invention is of a miniaturized chromatographic column, intended in use to be packed with a particulate chromatographic medium. A schematic of such a miniaturized chromatographic column is shown in FIG. 1.

Figure 1:
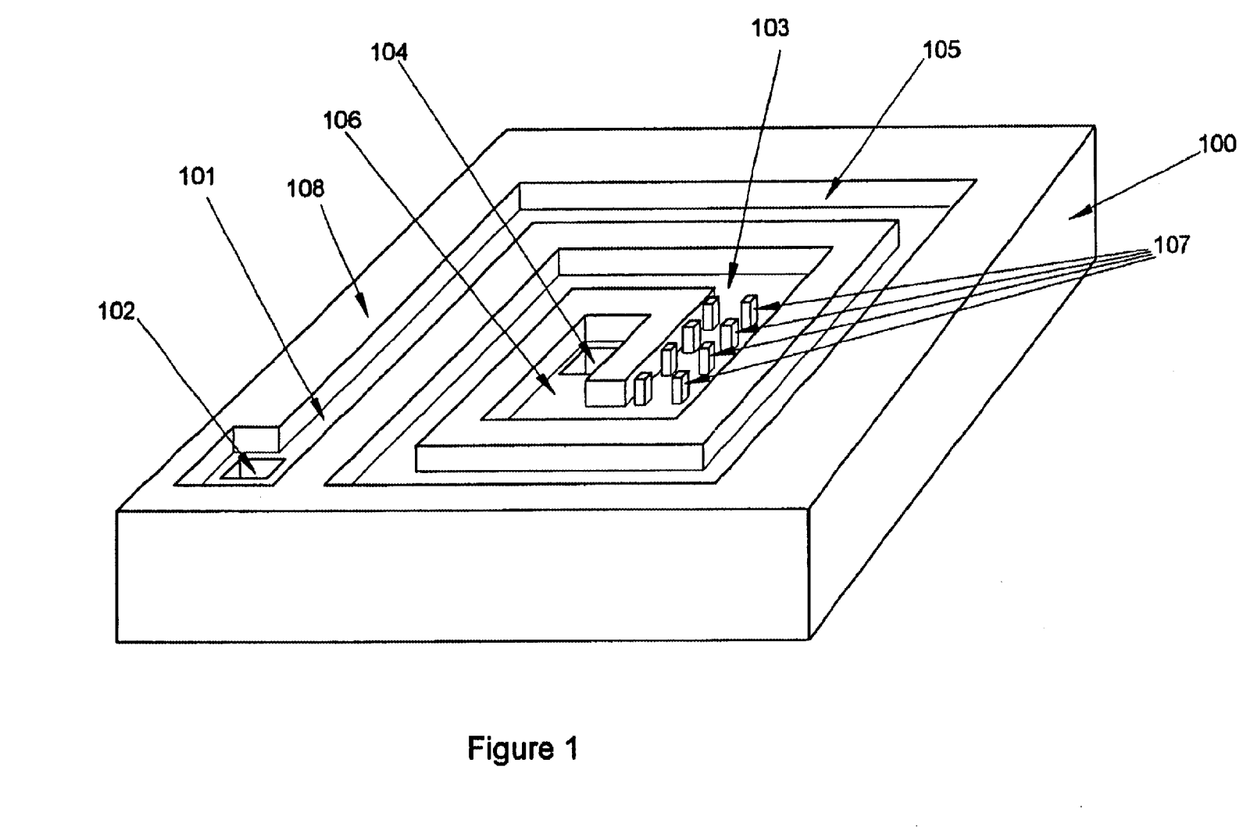
FIG. 1 shows an oblique schematic view of a first implementation of the instant invention.

In FIG. 1 appears a substrate 100, whose top surface has been configured to define a sealing plane 108, an elongated groove 101, a sample input aperture 102, a packing retainer 103, and a sample output aperture 104. In this implementation, the elongated groove 101 takes a square spiral path, and has a nominally quadrilateral cross section. The sample input aperture 102 and the sample output aperture 104 in this implementation penetrate substrate 100, thereby enabling access to the elongated groove 101 from the back side of the substrate. Other possibilities will be clear to one skilled in the art, some of which are illustrated in additional implementations described later.

A cover plate (not shown) is sealed atop substrate 100 so as to convert elongated groove 101 into an elongated column which is capable of confining a particulate chromatographic medium through which a mobile phase can be circulated. The sealing can be accomplished by a number of techniques, including welding, soldering, use of adhesives, anodic bonding, thermal fusion bonding, deformation sealing, and many others.

For the purpose of describing the instant invention, a packing retainer is defined as comprising a pattern of blocking elements so positioned within said elongated column, so that in a miniaturized chromatographic column packed with a particulate chromatographic medium, the packing retainer contributes only a small part of the total flow resistance of said column, and also so that the blocking elements substantially prevent passage of the particulate chromatographic medium through the packing retainer in response to the flow of the mobile phase through said column.

In the instant implementation, the packing retainer 103 divides the elongated groove 101 into a. stationary medium portion 105 and an output portion 106. The packing retainer 103 comprises a series of blocking elements 107, which are so positioned within the elongated groove 101 as to block passage of a particulate chromatographic medium (not shown) from stationary medium portion 105 into output portion 106. In the specific implementation illustrated in FIG. 1, the blocking elements 107 take the form of rectangular pillars placed in a simple square lattice pattern within elongated groove 101 so that the spaces between said blocking elements are smaller than the characteristic dimensions of the particles of chromatographic medium to be retained in stationary medium portion 105. It will be clear to one skilled in the art that many other blocking element shapes and patterns can be used to accomplish the retention function described above.

A miniaturized chromatographic column according to the instant invention will typically comprise a substrate 100 comprising crystalline or glassy semiconductors or insulators, as will the cover plate. The easiest materials to be used in implementation of the instant invention using conventional micromachining techniques include silicon crystal, amorphous silicon, and silicon oxide-containing glasses. However, many other materials can be so utilized, and can be required depending on the ultimate application of the device.

The features which are defined by the configuration of the top surface of the substrate 100 can be fabricated therein by etching said surface, e.g., using Bosch and other etching processes appropriate for forming the desired surface configuration in the material of the substrate. Other suitable fabrication techniques comprise mechanical machining of the substrate, e.g., using electron discharge machining or other suitable techniques, forming the desired surface configuration concurrent with forming the substrate itself, e.g., through casting or directed crystal growth, and use of thick film photodefinable materials, e.g., EPON SU-8 thick film photoresist. Finally, the negative of these features could be fabricated in one material by one of the above techniques, and then the desired features could be replicated in a second material using techniques such as hot embossing or injection molding.

Figure 2:
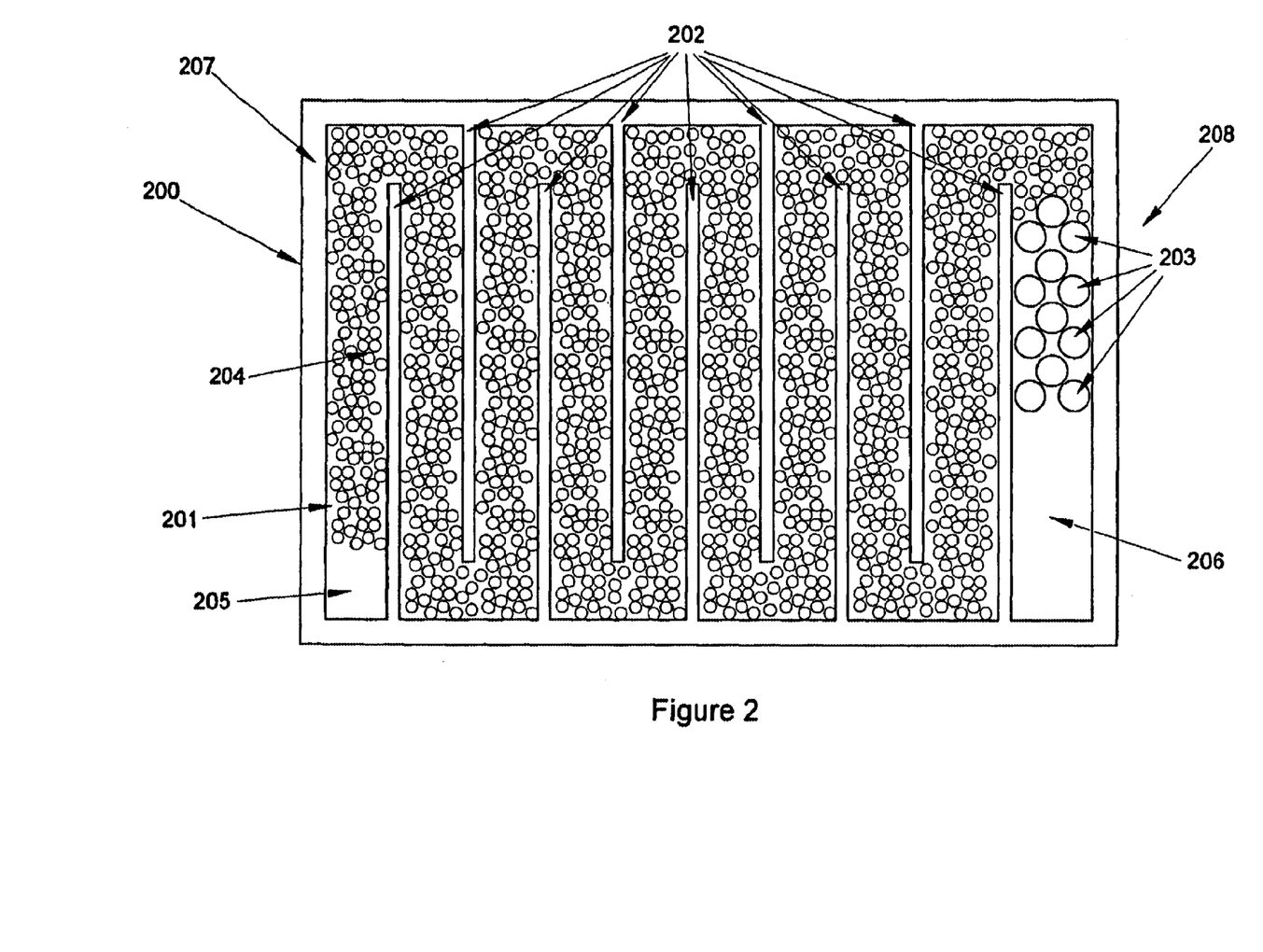
FIG. 2 shows a horizontal cross-sectional schematic view of a second implementation of the instant invention from above.

A different implementation of the instant invention is shown in FIG. 2, which is pictured from the top when the cover plate has been removed. In this implementation, the sample input aperture and the sample output aperture for the mobile phase are part of the cover plate, and hence are also not shown.

Substrate 200 has a top surface which has been configured so as to define a sealing plane 207, an elongated groove 201, and a packing retainer 208. In this implementation, elongated groove 201 follows a rectilinear serpentine path, where the groove is defined by groove walls 202.

Elongated groove 201 is divided into a stationary medium portion 205 and an output portion 206 by packing retainer 208, which comprises a pattern of blocking elements 203, said blocking elements 203 here taking the form of cylindrical pillars in a square lattice pattern. These cylindrical pillars are positioned so that a particulate chromatographic medium 204 cannot pass through the packing retainer 208, while at the same time presenting a small flow resistance to the flow of the mobile phase relative to the flow resistance of chromatographic medium 204.

Figure 3:
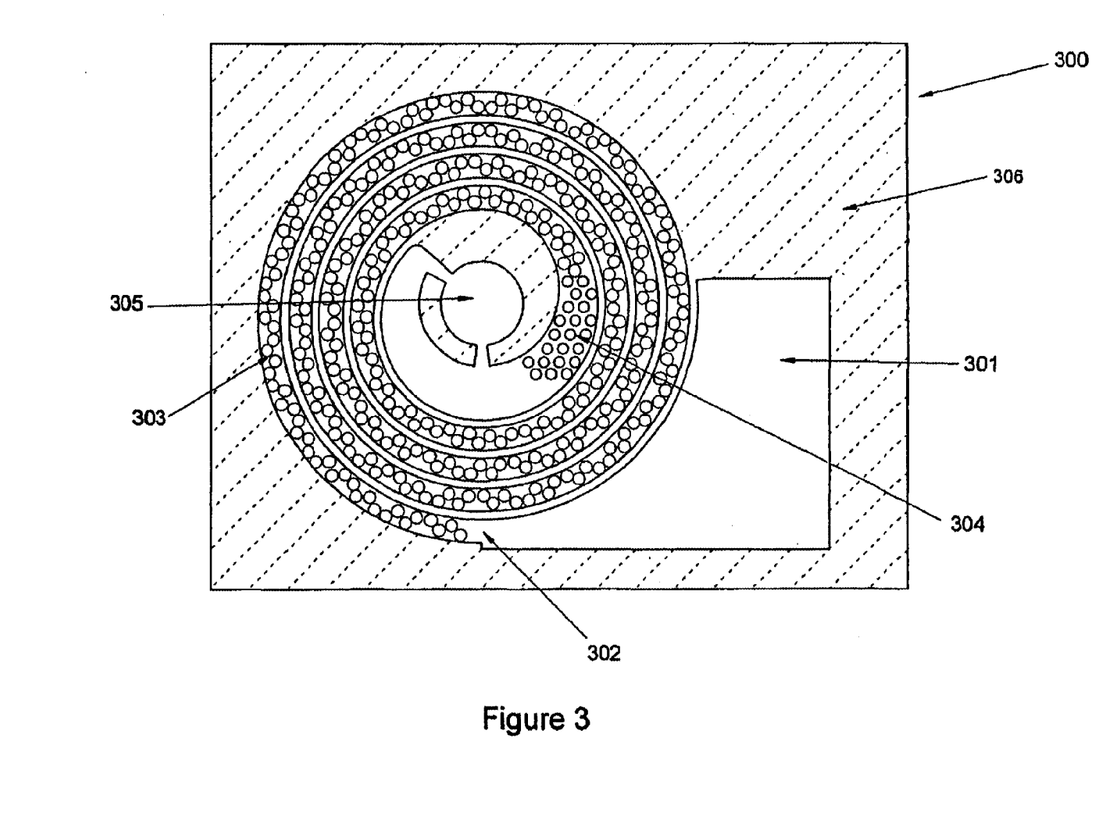
FIG. 3 shows a horizontal cross-sectional schematic view of a third implementation of the instant invention from above.

A third implementation of the instant invention is shown in FIG. 3, which is pictured in a top view after the cover plate has been removed. In this implementation, the sample input aperture and the sample output aperture for a mobile phase are part of the cover plate, and hence are also not shown.

Substrate 300 has a top surface which has been configured to define a sealing plane 306, an elongated groove 302 with a first end 301 and a second end 305, and a packing retainer 304. In this implementation, the elongated groove 302 takes a simple spiral shape between first end 301 and second end 305. This shape is easy to fabricate using silicon micromachining, and the relative lack of stress concentrators makes such a shape particularly robust.

A portion of elongated groove 302 located between the packing retainer 304 and the first end 301 contains particulate chromatographic medium 303. The packing retainer 304 comprises a pattern of blocking elements which are positioned so that particulate chromatographic medium 303 cannot pass through the packing retainer 304, while at the same time the packing retainer 304 presents a small flow resistance to the flow of the mobile phase relative to the flow resistance of chromatographic medium 303.

Figure 4:
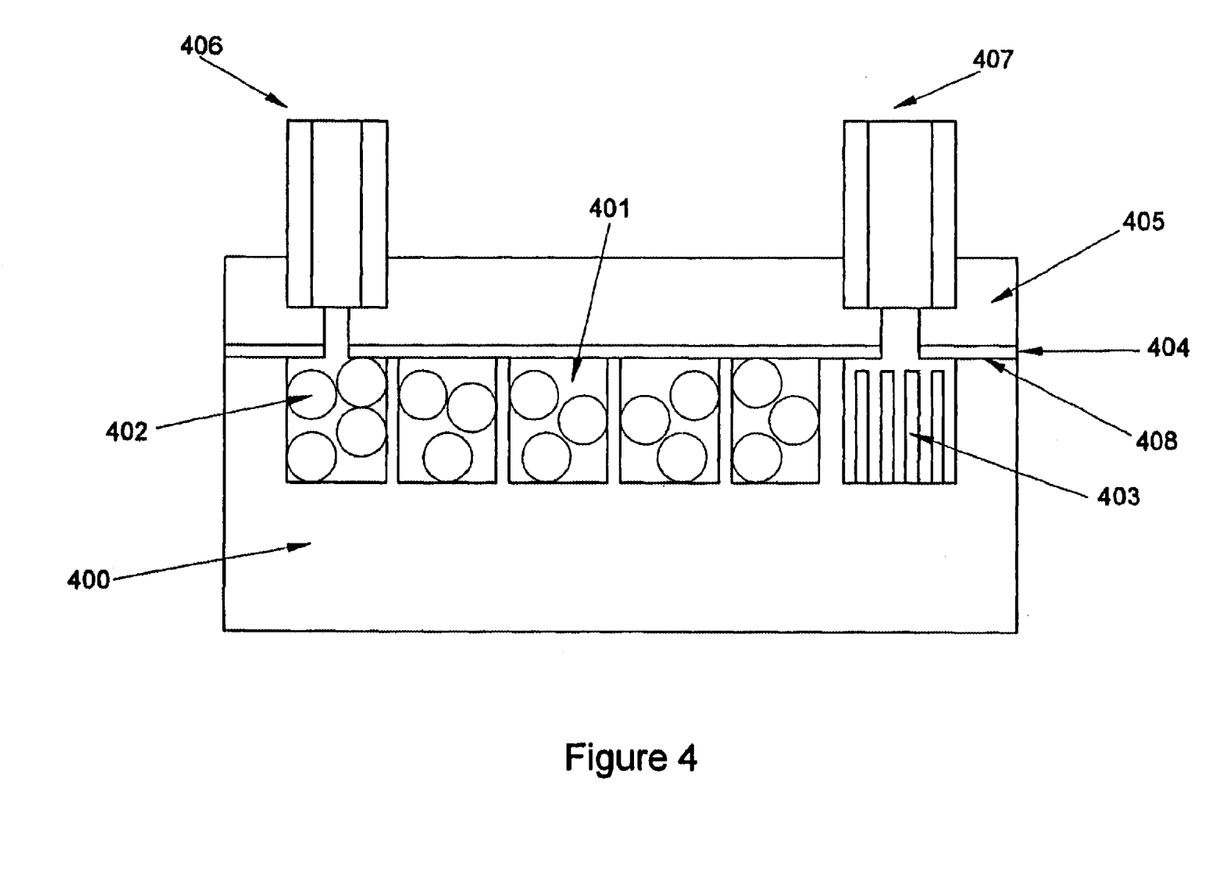
FIG. 4 shows a vertical cross-sectional schematic view of a fourth implementation of the instant invention from the side.

In FIG. 4, a vertical cross-section schematic view of an implementation of the instant invention is shown. Substrate 400 has been configured to define a sealing plane 408, an elongated column 401, and a packing retainer 403. A cover plate 405 has been sealed atop the substrate by sealant layer 404, which is disposed between sealing plane 408 and the bottom surface of cover plate 405.

Sealant layer 404 can comprise a region within which the materials of the substrate and the cover plate are mixed, as in welding or anodic bonding. Alternately, sealant layer 404 can comprise an added sealant material, such as an adhesive, solder, or a deformable material. Here the sealant layer 404 is shown as covering the entire bottom surface of the cover plate 405. However, it is only necessary that sufficient region be covered to insure effective sealing.

A path for the passage of the mobile phase through the miniaturized chromatographic column is formed by sample input aperture 406, elongated column 401, and sample output aperture 407. A particulate chromatographic medium 402 is disposed within the portion of elongated column 401 positioned between the sample input aperture 406 and the packing retainer 403.

It is often beneficial to include devices to measure and control the temperature of the chromatographic column. In FIG. 4, an integrated heating element 409 is formed on the back side of the substrate 400, and an integrated temperature probe 410 is formed on the cover plate 405. These locations are not special, but integrated heating element 409 is placed so as to produce a predetermined temperature profile within the chromatographic column, and integrated temperature probe 410 is placed so as to monitor said temperature profile. Integrated heating element 409 typically comprises a resistive heating element, comprising metal alloys or doped semiconductors. Integrated temperature probe 410 typically comprises a thermistor or a thermocouple. In some cases the functions of integrated heating element 409 and integrated temperature probe 410 can be subsumed into a single integrated component.

To use the miniaturized chromatographic columns of the instant invention, a particulate chromatographic medium must be introduced within the elongated column. There are a variety of techniques to do so, which were described in copending U.S. Provisional Application No. 60/336,127, filed on Nov. 2, 2001 by the instant inventors, and assigned to Sandia Corporation. However, some of these techniques require an entryway into the elongated column which can be accessed after the cover glass has been sealed onto the sealing plane. While the sample input aperture and the sample output aperture both provide an entryway into the elongated column, the packing retainer prevents a chromatographic medium from being introduced via the sample output aperture, and it can prove useful for the sample input aperture to be too small for the particles of chromatographic medium to pass through.

Accordingly, it can be beneficial to provide an additional medium filling aperture in the cover plate or in the substrate. Such a medium filling aperture, in this case penetrating the cover plate, is shown in FIG. 5.

Figure 5:
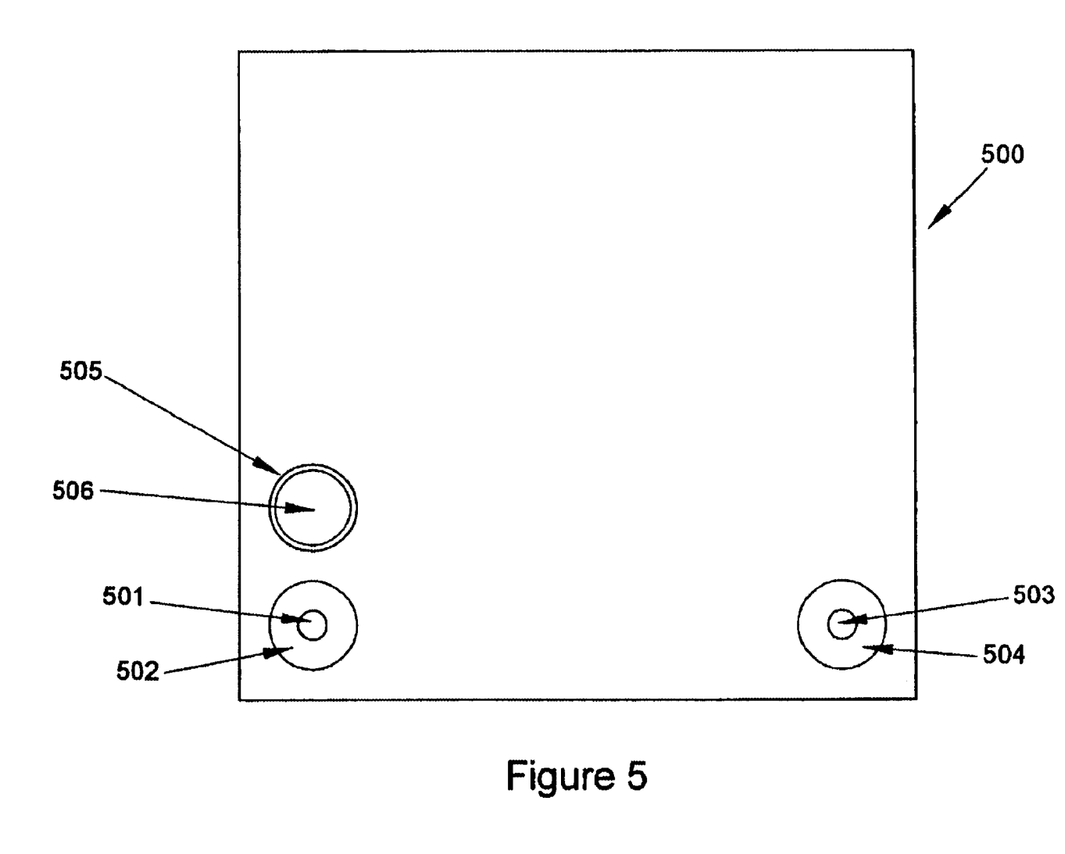
FIG. 5 shows a top view of an implementation of a cover plate for the instant invention.

FIG. 5 shows a top view of a cover plate 500, similar to cover plate 405 shown in the implementation of FIG. 4. A sample input aperture 501 penetrates cover plate 500, providing access to the stationary medium portion of the elongated column near the first end of the elongated groove in FIG. 4. Sample input aperture 501 is surrounded by input coupler recess 502, which provides a mounting place for an input coupling adapter (not shown). Similarly, a sample output aperture 503 penetrates cover plate 500, providing access to the output portion of the elongated column. Sample output aperture 503 is surrounded by output coupler recess 504, which provides a mounting place for an output coupling adapter (not shown).

Cover plate 500 also comprises a medium filling aperture 505. Medium filling aperture 505 penetrates cover plate 500, allowing access to the region of the elongated column which is to be filled with a particulate chromatographic medium. Medium filling aperture 505 is large enough to allow easy passage of said particulate chromatographic medium, and is sealed after the column is so filled, in this case by medium plug 506.

Applicants have successfully fabricated several miniaturized packed gas chromatograph columns according to the instant invention. These demonstration columns were fabricated on a silicon substrate using deep-reactive-ion silicon etching to configure the top surface of the substrate. The features created by this etching process included a spiral elongated groove, having walls with a thickness of about 25 microns, which define a square cross-section groove nominally 300 microns on a side. The length of the demonstration columns varied from 12 to 29 centimeters, with the longest column having a substrate footprint 1.3 centimeters on a side.

A packing retainer was also fabricated in the process of etching the substrate top surface. Within the elongated groove, and near one end of the groove, an array of cylindrical blocking elements was fabricated. These elements were the same height as the groove is deep, 50 microns in diameter, and positioned in an array with elements on 85 micron centers. Very few such blocking elements are required for effective retention of the particulate chromatographic medium, typically no more than 10 or 12, and typically requiring no more than about 150 microns length within the column.

A cover plate of silicate glass (Pyrex) was fabricated and sealed to the top surface of the silicon substrate using anodic bonding. The cover plate included machined holes allowing access to the input and output of the column by a mobile phase. The columns were packed with either a porous polymer packing medium having beads of roughly 60 micron diameter, or a porous carbon packing medium.

Some of the demonstration columns were tested by integrating them into a conventional gas chromatograph. This was accomplished by attaching them between the sample injector and a flame ionization detector within the oven space of the gas chromatograph. Chromatographic separations were carried out at 50° C. using a nitrogen mobile phase with a head pressure of 5 psi.

Figure 6:
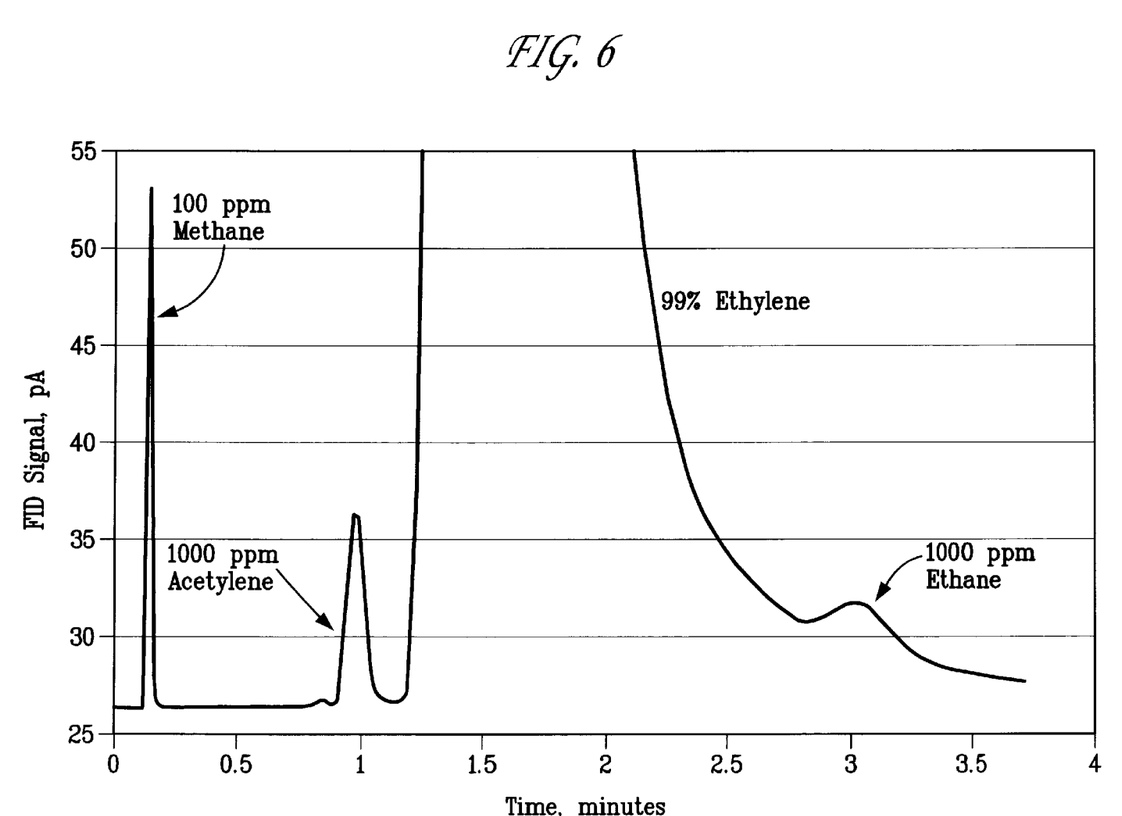
FIG. 6 shows data describing the separation and detection of hydrocarbon impurities in an ethylene gas sample using a microfabricated gas chromatographic column according to the instant invention.

FIG. 6 shows successful separation of volatile hydrocarbons relevant for ethylene processing as carried out by a microfabricated gas chromatographic column filled with particulate chromatographic media using a method according to the instant invention. As shown in FIG. 6, ethane, acetylene, and ethane impurities of 0.1% were easily detected in a gas sample which was predominantly composed of ethylene gas (about 99%).

Figure 7:
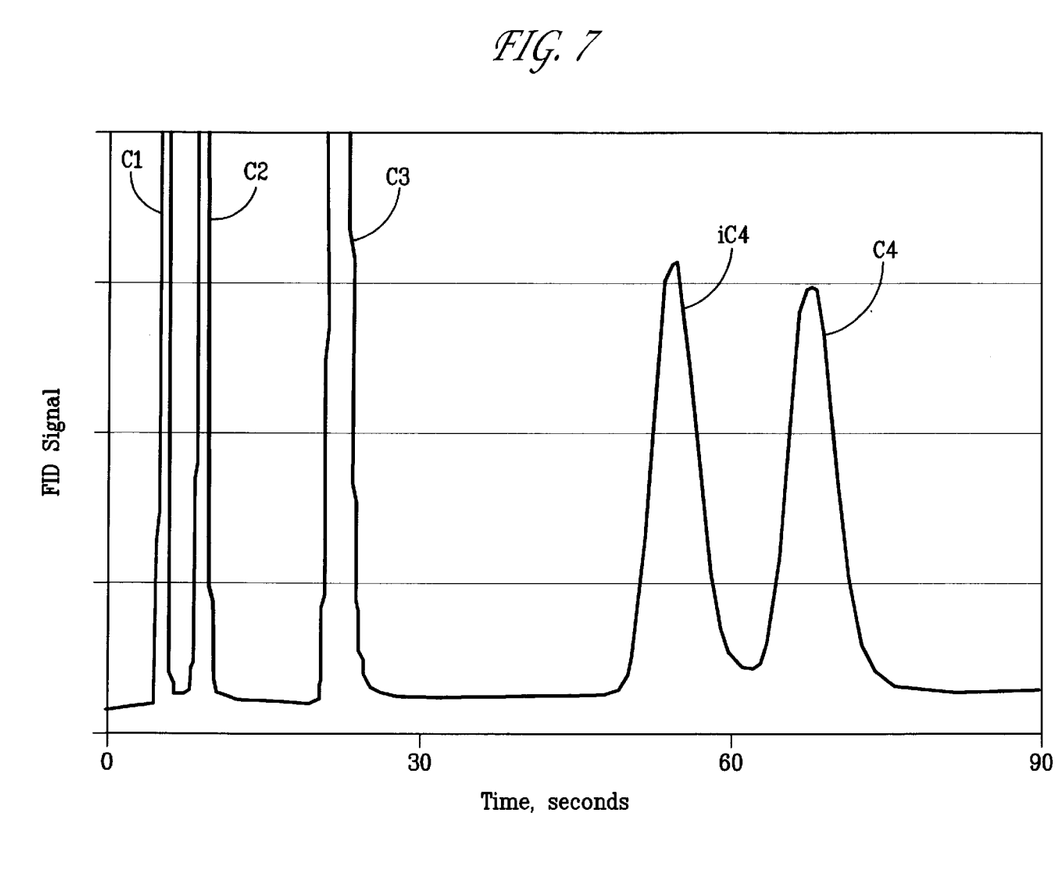
FIG. 7 shows data describing the separation and detection of hydrocarbon constituents of a model natural gas sample using a microfabricated gas chromatographic column according to the instant invention.

FIG. 7 shows successful separation of volatile hydrocarbons relevant for natural gas analysis as carried out by a microfabricated gas chromatographic column filled with particulate chromatographic media using a method according to the instant invention. As shown in FIG. 7, gas constituents with one, two, three, and four carbon atoms were cleanly separated by the chromatographic process, and branched four-carbon molecules were separated from linear four-carbon molecules.

We claim:

1. A miniaturized chromatographic column for packed particulate chromatographic media, comprising:
    a) a substrate comprising a surface configured to define a sealing plane, an elongated groove having a first end and a second end, and a packing retainer comprising a pattern of blocking elements positioned within the elongated groove and dividing said elongated groove into a stationary medium portion and an output portion;
    b) a cover plate sealed atop said sealing plane so as to convert said elongated groove into an elongated column;
    c) a sample input aperture so positioned as to permit a mobile phase to enter the stationary medium portion of said elongated column; and
    d) a sample output aperture so positioned as to permit the mobile phase to exit from the output portion of said elongated column.

2. The chromatographic column of claim 1, further comprising a packed particulate chromatographic medium disposed in the stationary medium portion of the elongated groove.

3. The chromatographic column of claim 2, wherein the length of the stationary medium portion of the elongated groove is in excess of ten centimeters.

4. The chromatographic column of claim 1, further comprising a sealant layer disposed between the cover plate and the sealing plane.

5. The chromatographic column of claim 4, wherein the sealant layer comprises an adhesive.

6. The chromatographic column of claim 4, wherein the sealant layer is deformed into the elongated groove.

7. The chromatographic column of claim 4, wherein the sealant layer comprises a region within which the materials of the substrate and the cover plate are mixed.

8. The chromatographic column of claim 7, wherein the sealant layer is formed by anodic bonding.

9. The chromatographic column of claim 1, wherein the elongated groove has a substantially quadrilateral cross-sectional shape.

10. The chromatographic column of claim 1, further comprising a medium filling aperture.

11. The chromatographic column of claim 10, further comprising a packed particulate chromatographic medium disposed in the stationary medium portion of the elongated groove.

12. The chromatographic column of claim 11, wherein the length of the stationary medium portion of the elongated groove is in excess of one meter, and the area of the sealing plane is less than 10 square centimeters.

13. The chromatographic column of claim 1, further comprising an integrated heating element.

14. The chromatographic column of claim 1, further comprising an integrated temperature probe.

* * * * *